(12) United States Patent
Aslan et al.

(10) Patent No.: US 7,786,302 B2
(45) Date of Patent: Aug. 31, 2010

(54) CRYSTALLINE FORMS OF VALACYCLOVIR HYDROCHLORIDE

(75) Inventors: Tuncer Aslan, Düzce (TR); A. Evren Ozarslan, Istanbul (TR); Filiz Sahbaz, Istanbul (TR); N. Sait Uluozyurt, Istanbul (TR); Nihat Arslan, Istanbul (TR)

(73) Assignee: Eczacibasi-Zentiva Kimyasal Urunler Sanayi Ve Ticaret A.S., Istanbul (TR)

( * ) Notice: Subject to any disclaimer, the term of this patent is extended or adjusted under 35 U.S.C. 154(b) by 55 days.

(21) Appl. No.: 10/558,243

(22) PCT Filed: May 30, 2003

(86) PCT No.: PCT/TR03/00048

§ 371 (c)(1),
(2), (4) Date: Nov. 23, 2005

(87) PCT Pub. No.: WO2004/106338

PCT Pub. Date: Dec. 9, 2004

(65) Prior Publication Data

US 2006/0252776 A1 Nov. 9, 2006

(51) Int. Cl.
*C07D 473/18* (2006.01)
*A61K 31/522* (2006.01)

(52) U.S. Cl. .................................................. 544/276

(58) Field of Classification Search ........................ None
See application file for complete search history.

(56) References Cited

U.S. PATENT DOCUMENTS

| | | | | |
|---|---|---|---|---|
| 4,199,574 A | * | 4/1980 | Schaeffer ..................... 514/81 |
| 4,957,924 A | * | 9/1990 | Beauchamp ............. 514/263.38 |
| 5,061,708 A | * | 10/1991 | Krenitsky .............. 514/263.38 |
| 5,831,075 A | * | 11/1998 | Jackson ................... 536/27.14 |
| 5,879,706 A | * | 3/1999 | Carter et al. ................ 424/464 |
| 6,107,302 A | * | 8/2000 | Carter et al. .......... 514/263.38 |
| 6,849,736 B2 | * | 2/2005 | Wizel et al. ................. 544/276 |
| 6,849,737 B2 | * | 2/2005 | Etinger et al. ............... 544/276 |
| 2003/0153757 A1 | * | 8/2003 | Etinger et al. ............... 544/276 |
| 2004/0197396 A1 | * | 10/2004 | Fain et al. .................... 424/464 |
| 2005/0043329 A1 | * | 2/2005 | Wizel et al. ............ 514/263.38 |
| 2005/0059684 A1 | * | 3/2005 | Dolitzky et al. ........ 514/263.38 |
| 2005/0070711 A1 | * | 3/2005 | Lifshitz et al. ............... 544/276 |
| 2005/0085491 A1 | * | 4/2005 | Lifshitz et al. ......... 514/263.38 |
| 2005/0130993 A1 | * | 6/2005 | Etinger et al. .......... 514/263.38 |
| 2005/0187229 A1 | * | 8/2005 | Wizel et al. ............ 514/263.38 |
| 2005/0192296 A1 | * | 9/2005 | Harel et al. ............ 514/263.38 |
| 2006/0229322 A1 | * | 10/2006 | Cid ......................... 514/263.38 |
| 2006/0252776 A1 | * | 11/2006 | Aslan et al. ............ 514/263.38 |
| 2007/0021444 A1 | * | 1/2007 | Pizzocaro .............. 514/263.38 |
| 2007/0093511 A1 | * | 4/2007 | Fain et al. .............. 514/263.38 |
| 2007/0112193 A1 | * | 5/2007 | Khunt et al. ................. 544/276 |

FOREIGN PATENT DOCUMENTS

| | | | |
|---|---|---|---|
| CN | 1686140 | * | 10/2005 |
| EP | 0 976 750 A1 | | 2/2000 |
| WO | WO 96/22291 A1 | | 7/1996 |
| WO | WO 9725989 A1 | * | 7/1997 |
| WO | WO 9727194 A1 | * | 7/1997 |
| WO | WO 9803553 A1 | * | 1/1998 |
| WO | WO 03/022209 A2 | | 3/2003 |
| WO | WO 2004052892 A1 | * | 6/2004 |
| WO | WO 2006035452 A1 | * | 4/2006 |

OTHER PUBLICATIONS

"Valaciclovir, Valacyclovir, 256U87, Valtrex®," Drugs of the Future, vol. 19, No. 7, 1994, pp. 708-709.
Bernstein, Joel, et al., "Concomitant Polymorphs," Angewandte Chemie International Edition, vol. 38, 1999, cover and pp. 3441-3461.
Beutner, Karl R., "Valacyclovir: a review of its antiviral activity, pharmacokinetic properties, and clinical efficacy," Antiviral Research, vol. 28, 1995, pp. 281-290.
Threlfall, Terence L., "Analysis of Organic Polymorphs, A Review," Analyst, vol. 120, Oct. 1995, pp. 2435-2460.

* cited by examiner

*Primary Examiner*—Mark L Berch
(74) *Attorney, Agent, or Firm*—Arent Fox LLP

(57) ABSTRACT

In this invention the novel polymorphs of the valacyclovir hydrochloride and methods for preparing these novel polymorphs are provided.

18 Claims, 7 Drawing Sheets

CRYSTALLINE FORMS OF VALACYCLOVIR HYDROCHLORIDE

CROSS-REFERENCE TO RELATED APPLICATION

This application is a National Stage entry of International Application No. PCT/TR2003/000048 filed May 30, 2003, the entire specification claims and drawings of which are incorporated herewith by reference.

BACKGROUND OF THE INVENTION

Valacyclovir is an amino acid derivative of the acyclovir which is an acyclic analog of natural nucleoside guanine. Acyclovir shows selective and strong antiviral activity, especially against herpes simplex viruses.

Acyclovir lacks 3'-hydroxyl group at the side chain and so terminates chain elongation step of the viral DNA during DNA replication. See, Goodman et al, in *The Pharmacological Basis of Therapeutics* 1193-1198 ($9^{th}$ ed. 1996). The chemical name of the acyclovir is 2-Amino-1,9-dihydro-9-[(2-hydroxyethoxy)methyl]-6H-purin-6-one] and the CAS Registry number is 59277-89-3. Formula I shows the chemical structure of acyclovir.

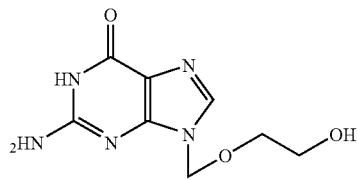

Formula 1

The chemical name of the valacyclovir hydrochloride is L-Valine 2-[(2-amino-1,6-dihydro-6-oxo-9H-purin-9-yl)methoxy]ethyl ester hydrochloride and the CAS Registry number is 124832-26-4. Formula II shows the chemical structure of valacyclovir hydrochloride.

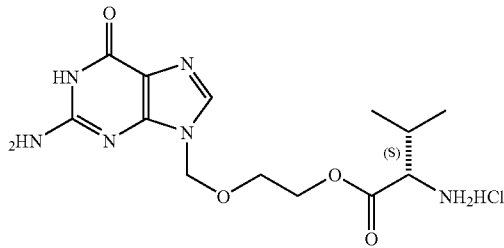

Formula 2

Although acyclovir shows strong antiviral activity (Schaeffer et al, *Nature* 1978, 272, 583), it is poorly absorbed from the gastrointestinal track. Because of this low bioavailability of acyclovir, multiple high doses of the oral drug must be taken.

However α-amino group of the valacyclovir can form hydrochloride salt and this increases the solubility and bioavailability of the drug without loosing its antiviral activity (see, for example U.S. Pat. No. 4,957,924 ).

Valacyclovir hydrochloride is prepared following the basic patent EP 0308 065. Preparation of an anhydrous form of valacyclovir hydrochloride is described in U.S. Pat. No. 6,107,302. In another patent application (WO 03/022209 A2) more polymorphs of the antiviral valacyclovir hydrochloride are reported.

Discovery of the new crystalline forms of the active pharmaceuticals provides new possibilities for the formulation studies and can increase the stability of the active ingredients.

SUMMARY OF THE INVENTION

It is an aspect of the present invention to provide novel polymorphs VIII, IX, X, XI, XII, XIII, and XIV of valacyclovir hydrochloride and as well as admixtures of two or more of these forms.

It is another aspect of the invention to provide procedures for the preparation of the crystalline forms VIII, IX, X, XI, XII, XIII, and XIV.

It is one aspect, the present invention relates to valacyclovir hydrochloride in form VIII characterized by x-ray diffraction peaks (reflections) at about 3.5, 6.6, 9.2, 14.3, 15.6, 16.2, 16.5, 16.9, 19.0, 19.9, 21.3, 22.8, 24.0, 26.7, 27.2, and 27.8±2 degrees two theta.

Figure 1:
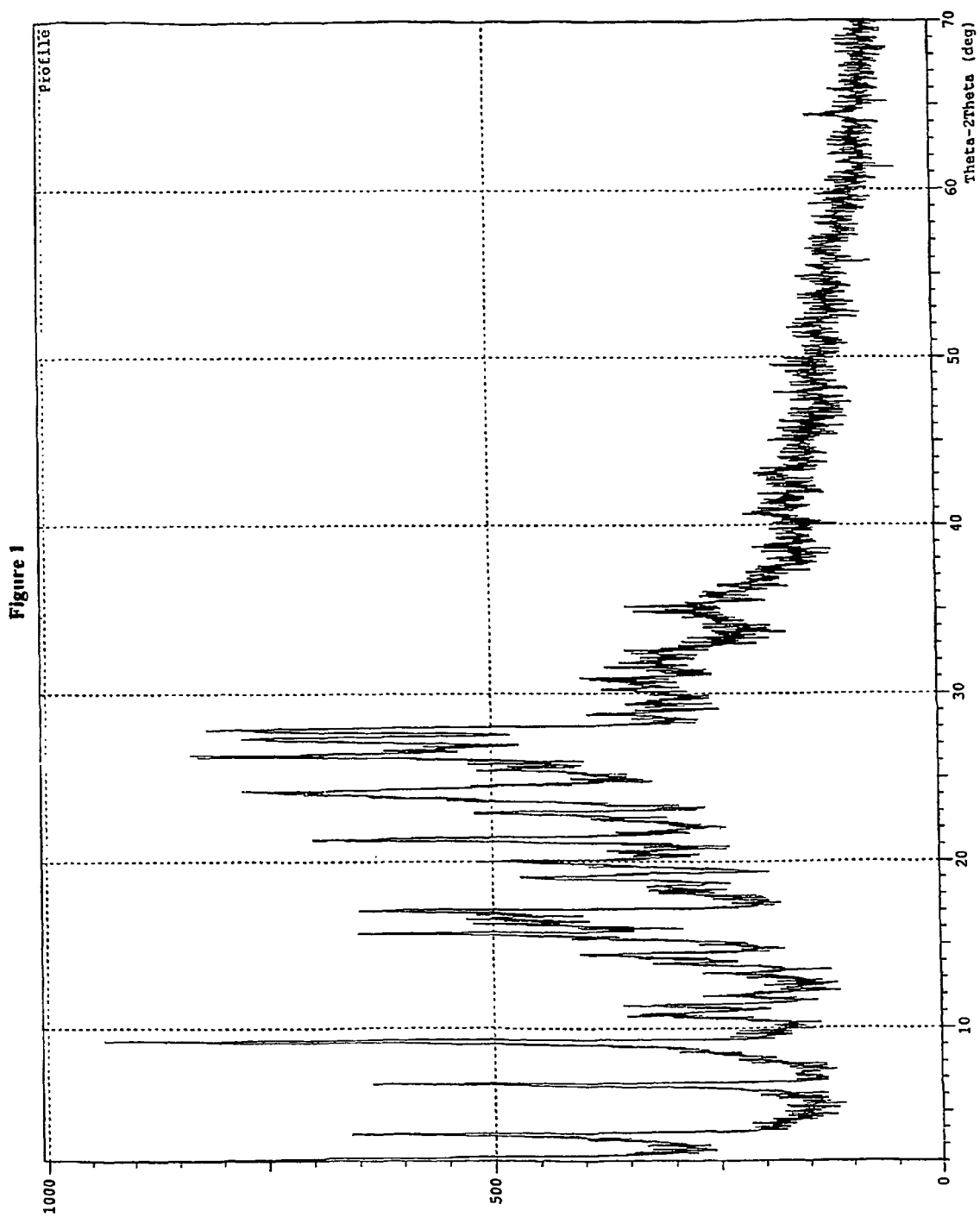
FIG. 1 shows a representative x-ray diffraction pattern of valacyclovir hydrochloride in form VIII.

In another aspect, the present invention also relates to valacyclovir hydrochloride in form VIII having x-ray powder diffraction pattern as shown in FIG. 1.

It is also an aspect, the present invention relates to valacyclovir hydrochloride in form VIII having the water content between about 0.1% to 10%, particularly between about 0.5% to 3% determined by Karl Fischer analysis.

It is one aspect, the present invention relates to valacyclovir hydrochloride in form IX characterized by x-ray diffraction peaks (reflections) at about 3.6, 7.0, 8.5, 9.4, 10.6, 10.8, 13.2, 15.4, 16.4, 20.1, 20.8, 21.3, 23.8, 24.6, 25.9, 26.3, 26.7, 27.2 and 27.8±2 degrees two theta.

Figure 2:
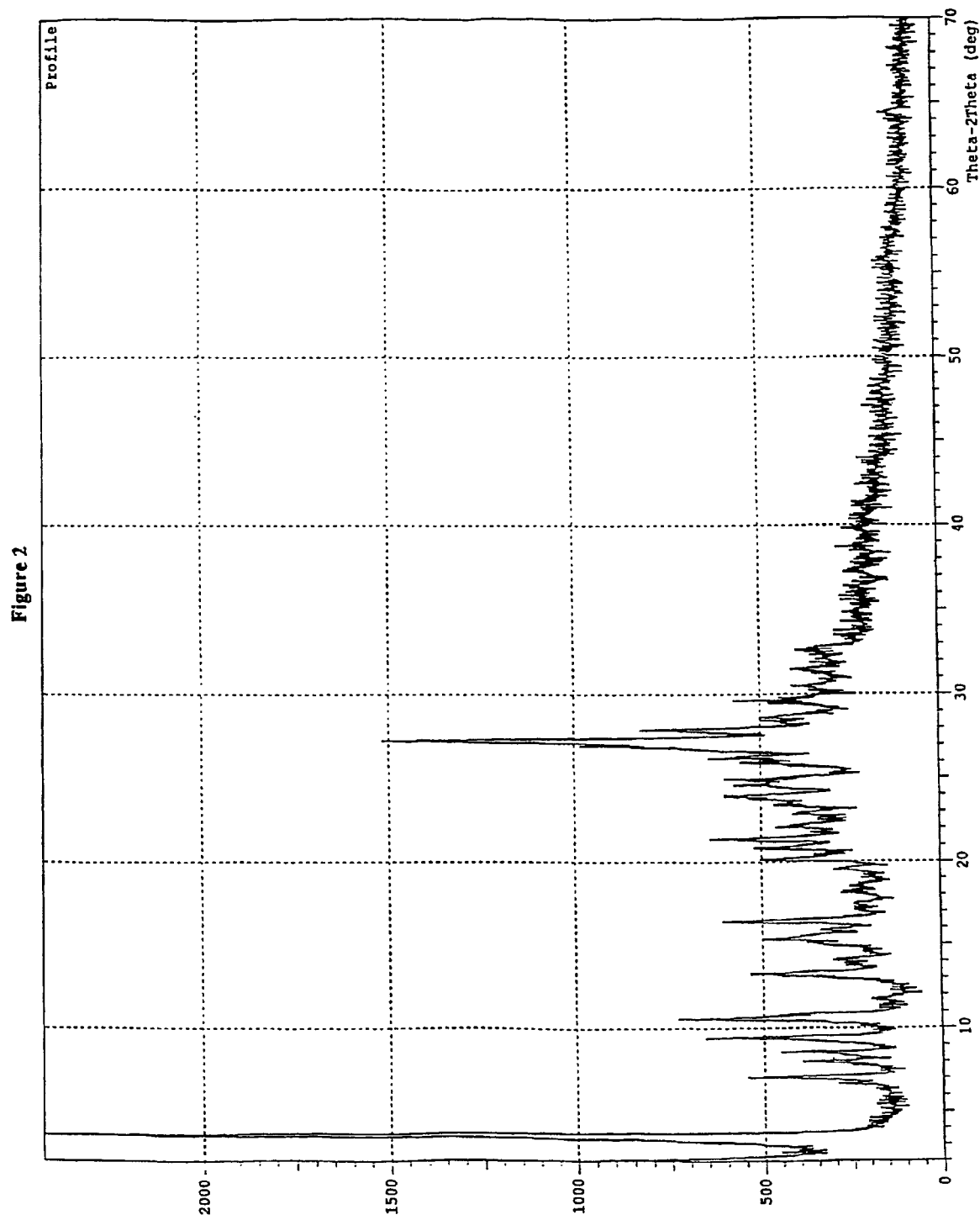
FIG. 2 shows a representative x-ray diffraction pattern of valacyclovir hydrochloride in form IX.

In another aspect, the present invention also relates to valacyclovir hydrochloride in form IX having x-ray powder diffraction pattern as shown in FIG. 2.

It is also an aspect, the present invention relates to valacyclovir hydrochloride in form IX having the water content between about 0.1% to 10%, particularly between about 6% to 10% determined by Karl Fischer analysis.

Figure 3:
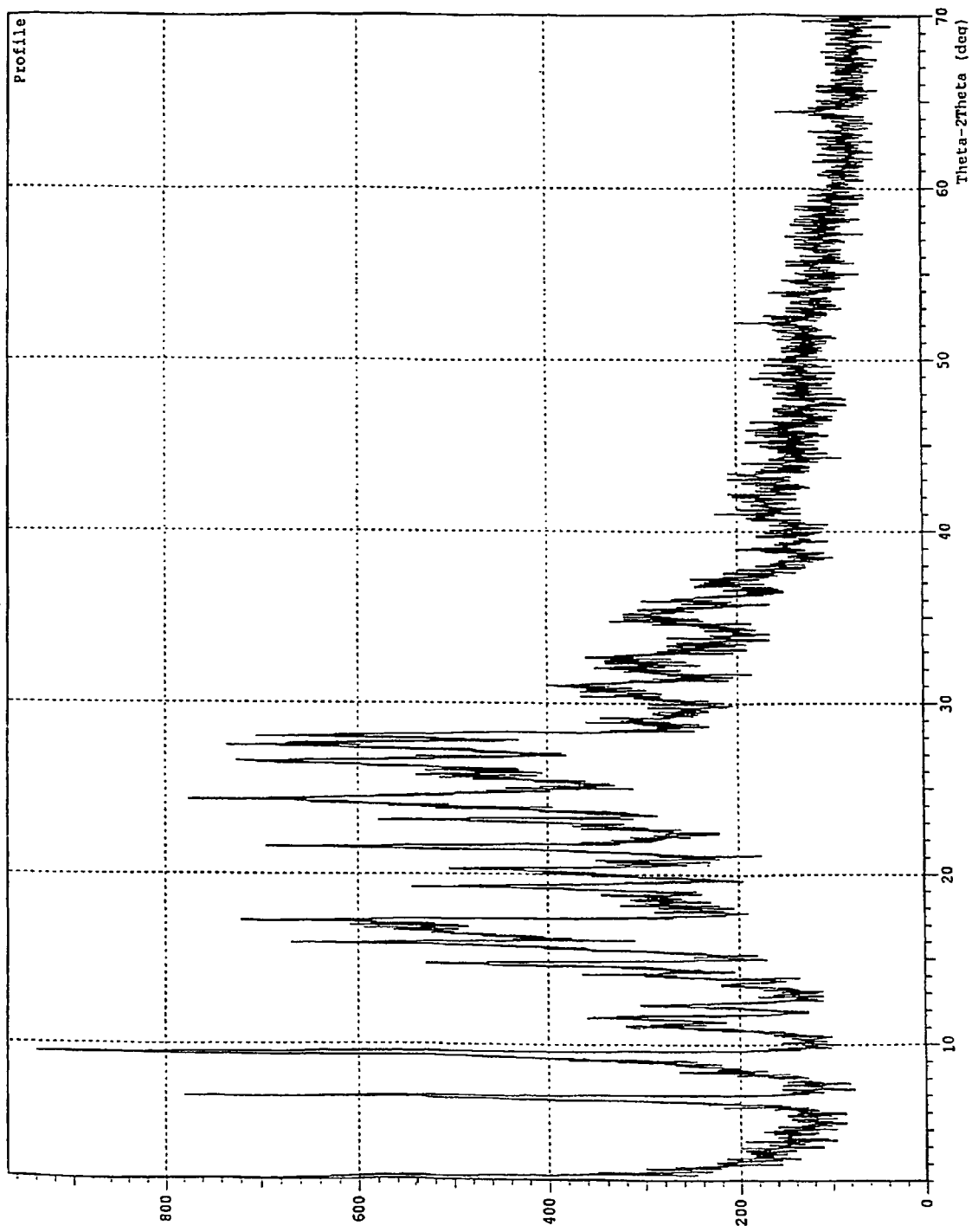
FIG. 3 shows a representative x-ray diffraction pattern of valacyclovir hydrochloride in form X.

It is one aspect, the present invention relates to valacyclovir hydrochloride in form X characterized by x-ray diffraction peaks (reflections) at about 6.9, 9.4, 11.6, 14.7, 15.9, 16.7, 17.2, 19.2, 21.5, 23.1, 24.2, 26.5, 27.5, and 28.0±2 degrees two theta. In another aspect, the present invention also relates to valacyclovir hydrochloride in form X having x-ray powder diffraction pattern as shown in FIG. 3.

It is also an aspect, the present invention relates to valacyclovir hydrochloride in form X having the water content between about 0.1% to 10%, particularly between about 3% to 7% determined by Karl Fischer analysis.

It is one aspect, the present invention relates to valacyclovir hydrochloride in form XI characterized by x-ray diffraction peaks (reflections) at about 6.7, 9.3, 11.1, 12.2, 14.6, 15.9, 16.7, 20.1, 21.6, 23.0, 24.1, 26.1, 27.3, 30.6, and 32.0±2 degrees two theta.

Figure 4:
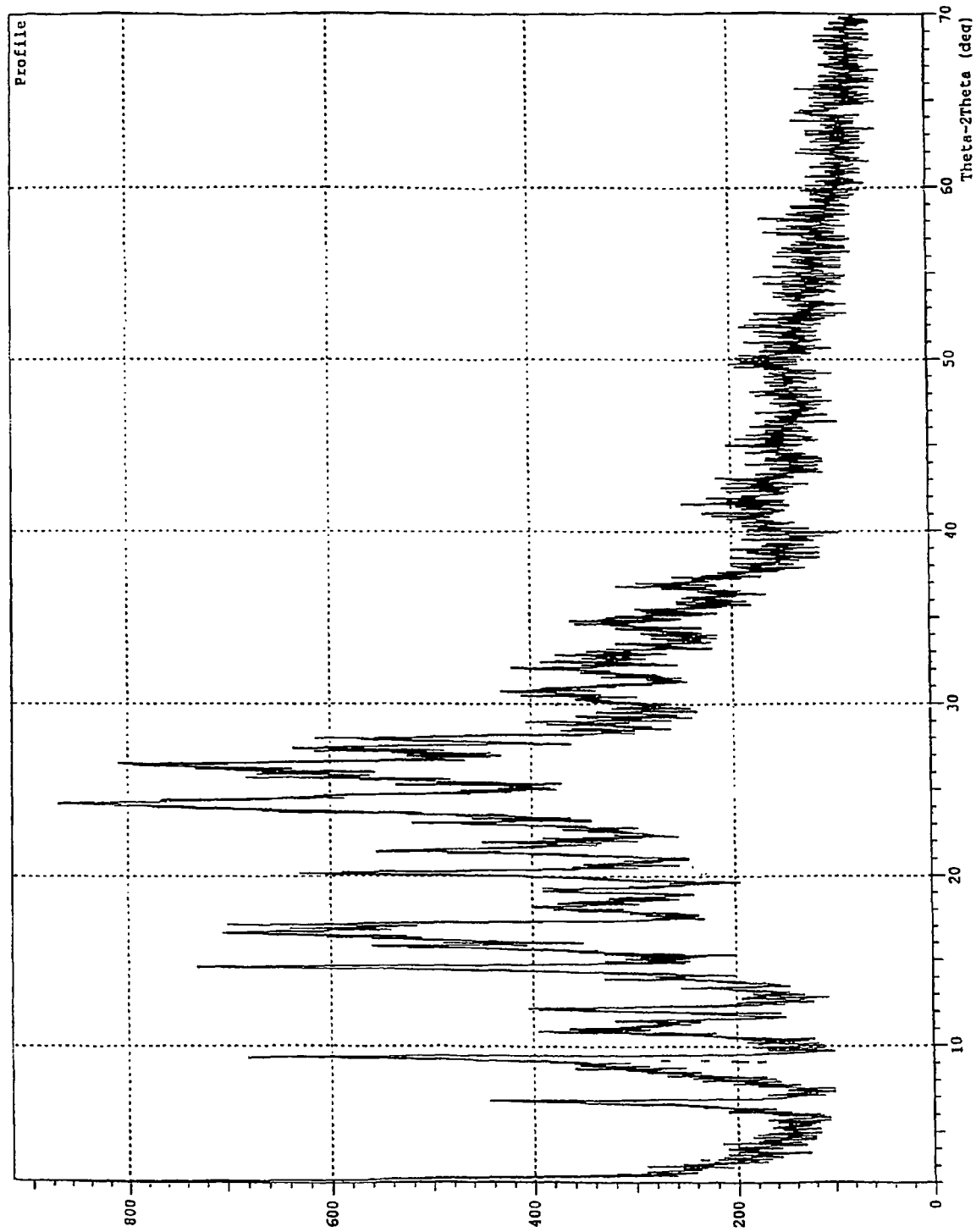
FIG. 4 shows a representative x-ray diffraction pattern of valacyclovir hydrochloride in form XI.

In another aspect, the present invention also relates to valacyclovir hydrochloride in form XI having x-ray powder diffraction pattern as shown in FIG. 4.

It is also an aspect, the present invention relates to valacyclovir hydrochloride in form XI having the water content between about 0.1% to 10%, particularly between about 1% to 3% determined by Karl Fischer analysis.

It is one aspect, the present invention relates to valacyclovir hydrochloride in form XII characterized by x-ray diffraction peaks (reflections) at about 6.9, 9.5, 11.6, 15.6, 15.8, 17.2, 19.3, 21.6, 23.1, 26.6, 27.6, and 28.1±2 degrees two theta.

Figure 5:
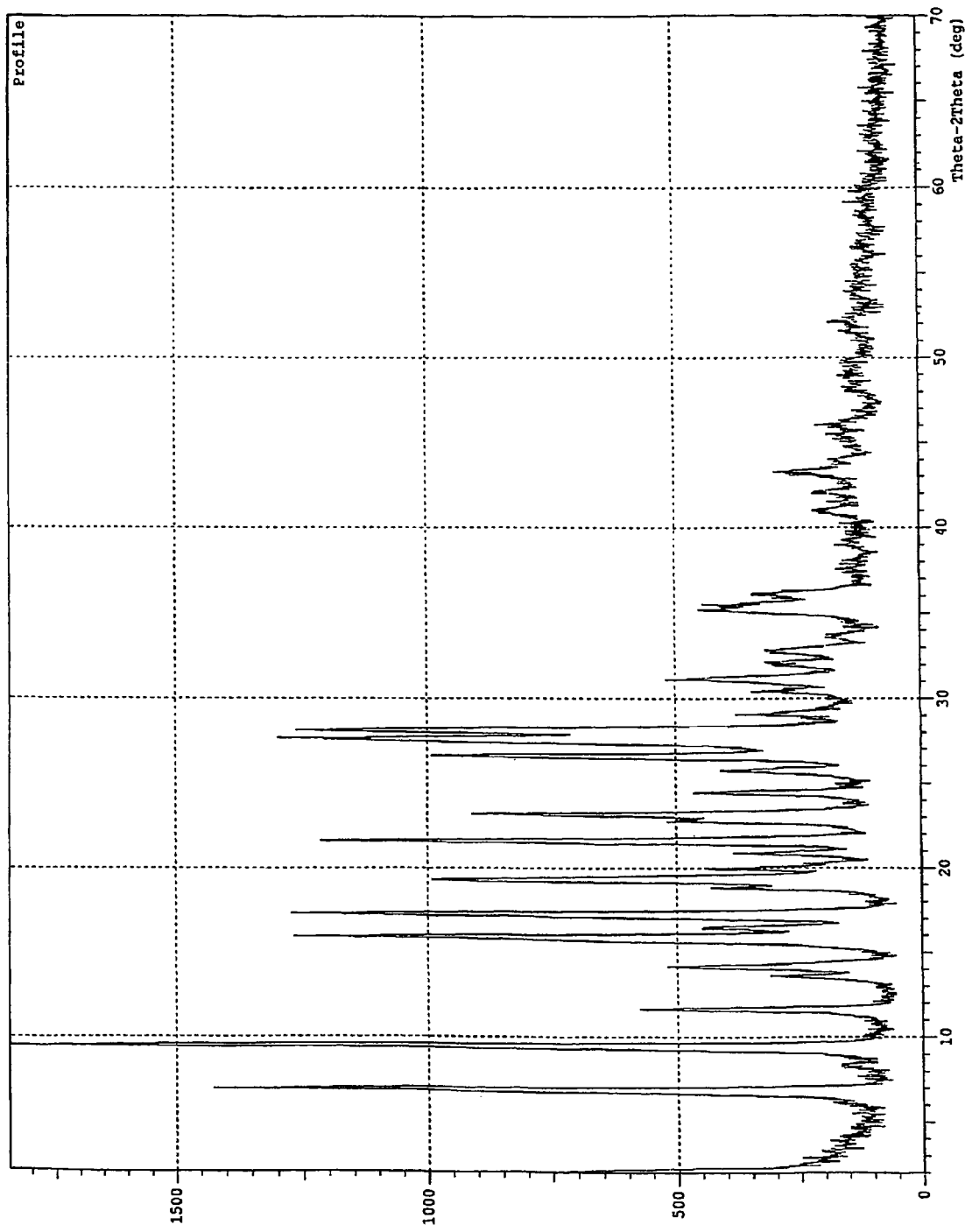
FIG. 5 shows a representative x-ray diffraction pattern of valacyclovir hydrochloride in form XII.

In another aspect, the present invention also relates to valacyclovir hydrochloride in form XII having x-ray powder diffraction pattern as shown in FIG. 5.

It is also an aspect, the present invention relates to valacyclovir hydrochloride in form XII having the water content between about 0.1% to 10%, particularly between about 0.5% to 9% determined by Karl Fischer analysis.

It is one aspect, the present invention relates to valacyclovir hydrochloride in form XIII characterized by x-ray diffraction peaks (reflections) at about 3.6, 6.6, 9.2, 15.4, 15.6, 16.9, 19.0, 21.3, 22.8, 26.3, 27.2, and 27.8±2 degrees two theta.

Figure 6:
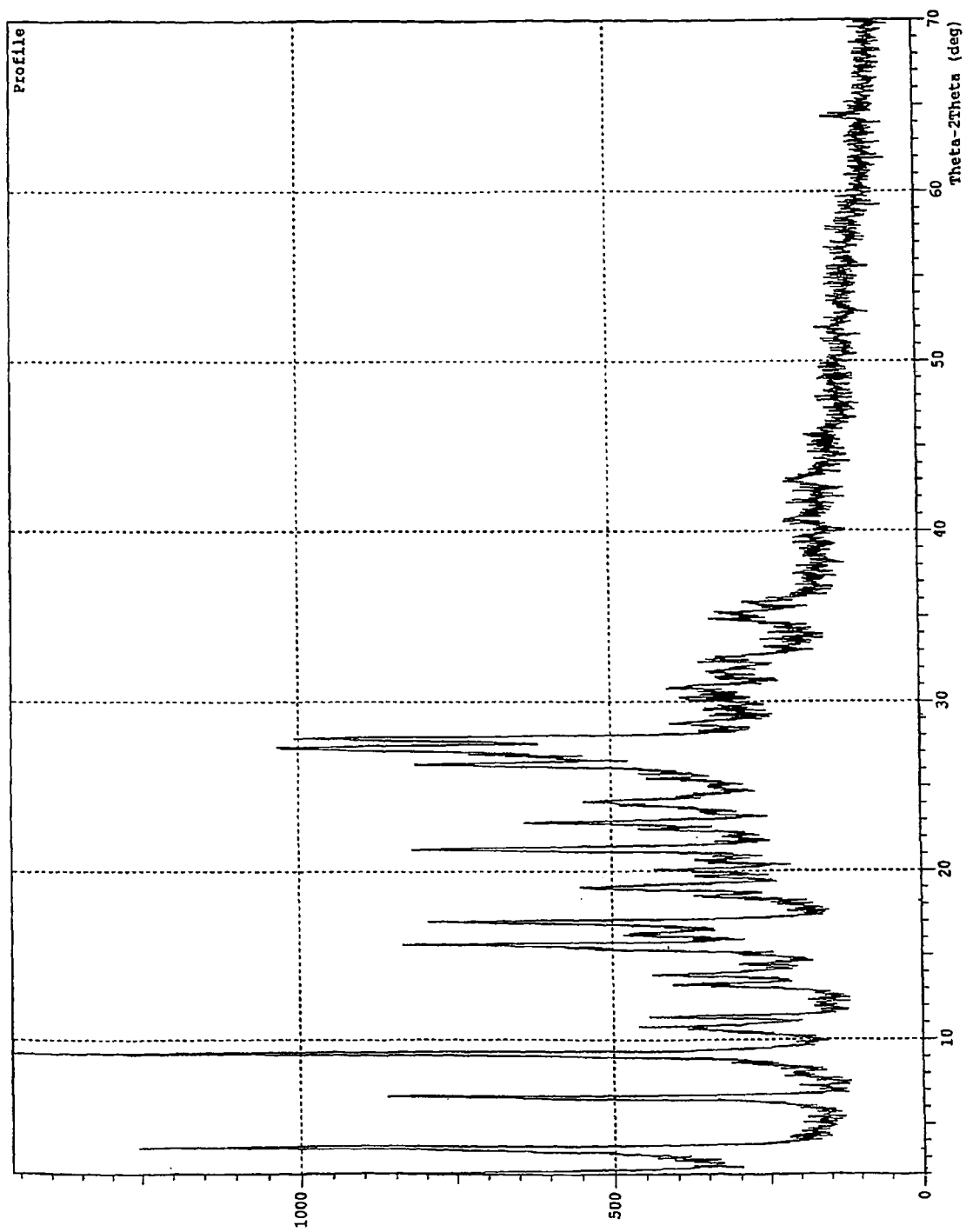
FIG. 6 shows a representative x-ray diffraction pattern of valacyclovir hydrochloride in form XIII.

In another aspect, the present invention also relates to valacyclovir hydrochloride in form XIII having x-ray powder diffraction pattern as shown in FIG. 6.

It is also an aspect, the present invention relates to valacyclovir hydrochloride in form XIII having the water content between about 0.1% to 10%, particularly between about 3% to 5% determined by Karl Fischer analysis.

It is one aspect, the present invention relates to valacyclovir hydrochloride in form XIV characterized by x-ray diffraction peaks (reflections) at about 3.3, 3.6, 6.7, 9.3, 9.5, 10.6, 10.9, 13.3, 15.3, 15.7, 16.4, 20.1, 21.4, 24.0, 26.3, 26.9, 27.2, and 27.9±2 degrees two theta.

Figure 7:
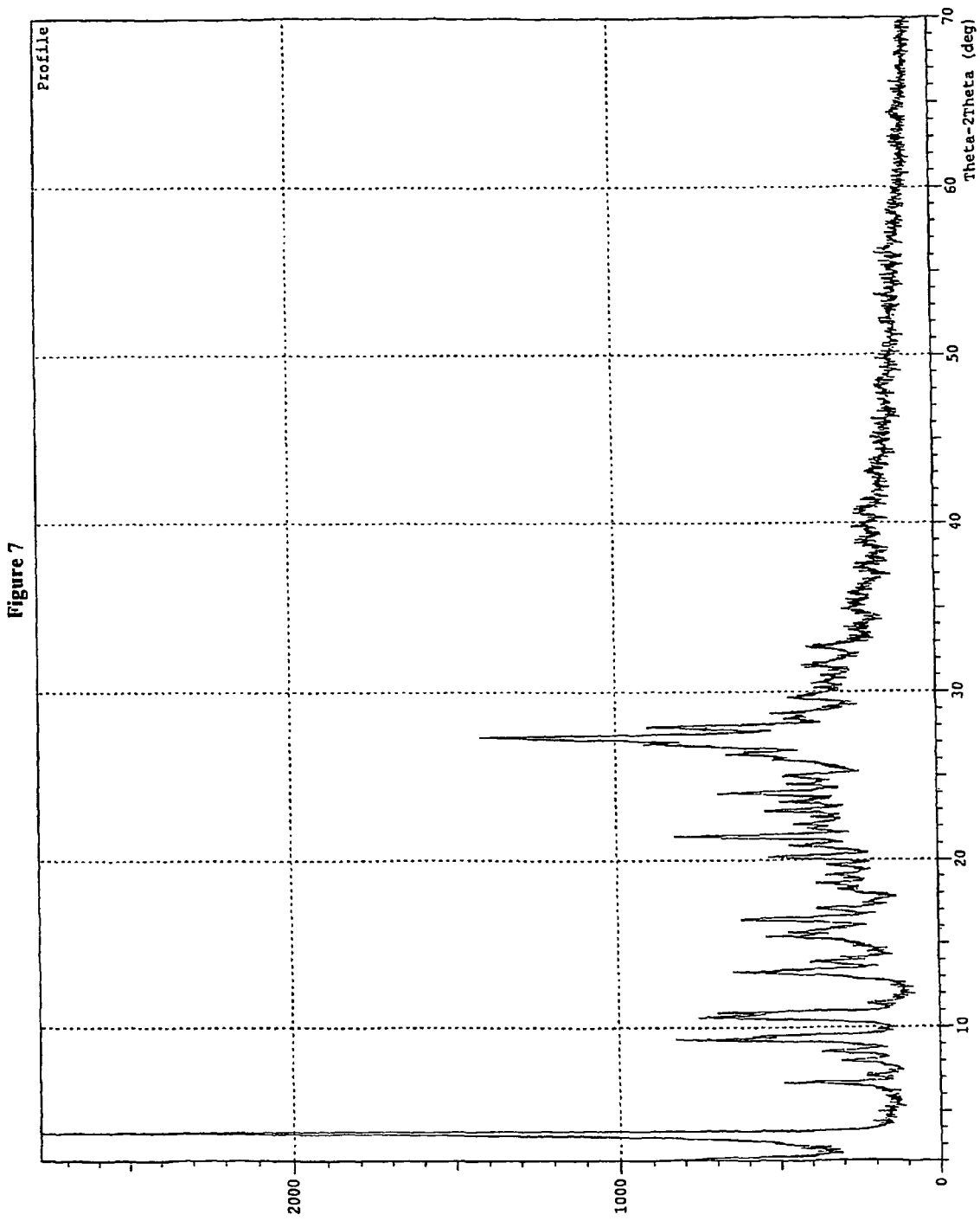
FIG. 7 shows a representative x-ray diffraction pattern of valacyclovir hydrochloride in form XIV.

In another aspect, the present invention also relates to valacyclovir hydrochloride in form XIV having x-ray powder diffraction pattern as shown in FIG. 7.

It is also an aspect, the present invention relates to valacyclovir hydrochloride in form XIV having the water content between about 0.1% to 10%, particularly between about 6% to 9% determined by Karl Fischer analysis.

In another aspect, the present invention relates to a process for preparing valacyclovir hydrochloride form VIII, including the step of dissolving valacyclovir hydrochloride in dimethylformamide (DMF) and precipitating by adding ethyl acetate then isolating valacyclovir hydrochloride in form VIII from this mixture.

It is another aspect, carrying the experiment at a temperature between about −10 to 18° C., particularly between about 0 to 5° C. and drying the valacyclovir hydrochloride form VIII at a temperature between about 20 to 80° C.

In another aspect, the present invention relates to a process for preparing valacyclovir hydrochloride form IX, including the step of dissolving valacyclovir hydrochloride in methanol and precipitating by adding n-hexanes then isolating valacyclovir hydrochloride in form IX from this mixture.

It is another aspect, carrying the experiment at a temperature between about −10 to 18° C., particularly between about 0 to 5° C. and drying the valacyclovir hydrochloride form IX at a temperature between about 20 to 80° C.

In another aspect, the present invention relates to a process for preparing valacyclovir hydrochloride form X, including the step of dissolving valacyclovir hydrochloride in dimethylformamide (DMF) and precipitating by adding acetone then isolating valacyclovir hydrochloride in form X from this mixture.

It is another aspect, carrying the experiment at a temperature between about 20 to 60° C., particularly between about 20 to 30° C. and drying the valacyclovir hydrochloride form X at a temperature between about 20 to 80° C. particularly about 45 to 55° C.

In another aspect, the present invention relates to a process for preparing valacyclovir hydrochloride form XI, including the step of dissolving valacyclovir hydrochloride in dimethylformamide (DMF) and precipitating by adding ethyl acetate then isolating valacyclovir hydrochloride in form XI from this mixture.

It is another aspect, carrying the experiment at a temperature between about 20 to 60° C., particularly between about 20 to 30° C. and drying the valacyclovir hydrochloride form XI at a temperature between about 20 to 80° C. particularly about 45 to 55° C.

In another aspect, the present invention relates to a process for preparing valacyclovir hydrochloride form XII, including the step of dissolving valacyclovir hydrochloride in dimethylformamide (DMF) or in methanol and precipitating by adding acetone, diethylether or n-hexanes then isolating valacyclovir hydrochloride in form XII from this mixture.

It is another aspect, carrying the experiment at a temperature between about 20 to 70° C., particularly between about 20 to 65° C. and drying the valacyclovir hydrochloride form XII at a temperature between about 20 to 80° C. particularly about 45 to 55° C.

In another aspect, the present invention relates to a process for preparing valacyclovir hydrochloride form XIII, including the step of dissolving valacyclovir hydrochloride in dimethylformamide (DMF) and precipitating by adding acetone then isolating valacyclovir hydrochloride in form XIII from this mixture.

It is another aspect, carrying the experiment at a temperature between about −10 to 25° C., particularly between about 0 to 5° C. and drying the valacyclovir hydrochloride form XIII at a temperature between about 20 to 80° C. particularly about 45 to 55° C.

In another aspect, the present invention relates to a process for preparing valacyclovir hydrochloride form XIV, including the step of dissolving valacyclovir hydrochloride in methanol and precipitating by adding acetone then isolating valacyclovir hydrochloride in form XIV from this mixture.

It is another aspect, carrying the experiment at a temperature between about 20 to 60° C., particularly between about 20 to 30° C. and drying the valacyclovir hydrochloride form XIV at a temperature between about 20 to 80° C. particularly about 45 to 55° C.

DETAILED DESCRIPTION OF THE INVENTION

The present invention provides novel polymorphs VII, IX, X, XI, XII, XIII, and XIV of valacyclovir hydrochloride and as well as admixtures of two or more of these forms.

The invention also provides procedures for the preparation of the crystalline forms VIII, IX, X, XI, XII, XIII, and XIV as well as admixtures of two or more of these forms.

A Schmadzu RDX 6000 x-ray diffractometer is used for the measurements of x-ray diffractograms. The scanning range was 2-70 degrees two-theta. The samples were grounded before analysis.

The water content of the crystalline forms (polymorphs and pseudo-polymorphs) is measured by using Karl Fischer instrument following method given in the 1990 US Pharmacopoeia at pages 1619-1621 and in European Pharmacopoeia (1992, part 2, sixteen fascicule at v.3. 5. 6-1).

According to HPLC analysis, initially used valacyclovir hydrochloride which produced following EP 308 065 has a purity of more than 99.5% (based on area %).

The present invention provides a method for producing valacyclovir hydrochloride in form VIII which comprises the step of dissolving valacyclovir hydrochloride in DMF with stirring for 10-60 minutes at a temperature between about 20-25° C. and cooling to 0-5° C., then precipitating by adding acetone and stirring for another 10-60 minutes at this temperature. The solid so formed is isolated by filtration. The material is dried under reduced pressure at a temperature between about 20° C. to about 80° C., preferably at 50° C. for 15 hours. The product obtained following this procedure is valacyclovir hydrochloride in form VIII according to x-ray diffraction analysis.

The present invention provides a method for producing valacyclovir hydrochloride in form IX which comprises the step of dissolving valacyclovir hydrochloride in methanol with stirring for 10-60 minutes at a temperature between about 20-80° C., preferably at 65° C. and cooling to 0-5° C., then precipitating by adding n-hexanes and stirring for another 10-60 minutes at this temperature. The solid so formed is isolated by filtration. The material is dried under reduced pressure at a temperature between about 20° C. to about 80° C., preferably at 50° C. for 15 hours. The product obtained following this procedure is valacyclovir hydrochloride in form IX according to x-ray diffraction analysis.

The present invention provides a method for producing valacyclovir hydrochloride in form X which comprises the step of dissolving valacyclovir hydrochloride in DMF with stirring for 10-60 minutes at a temperature between about 20-25° C., then precipitating by adding acetone and stirring for another 10-60 minutes at this temperature. The solid so formed is isolated by filtration. The material is dried under reduced pressure at a temperature between about 20° C. to about 80° C., preferably at 50° C. for 15 hours. The product obtained following this procedure is valacyclovir hydrochloride in form X according to x-ray diffraction analysis.

The present invention provides a method for producing valacyclovir hydrochloride in form XI which comprises the step of dissolving valacyclovir hydrochloride in DMF with stirring for 10-60 minutes at a temperature between about 20-25° C., then precipitating by adding ethyl acetate and stirring for another 10-60 minutes at this temperature. The solid so formed is isolated by filtration. The material is dried under reduced pressure at a temperature between about 20° C. to about 80° C., preferably at 50° C. for 15 hours. The product obtained following this procedure is valacyclovir hydrochloride in form XM according to x-ray diffraction analysis.

The present invention provides a method for producing valacyclovir hydrochloride in form XII which comprises the step of dissolving valacyclovir hydrochloride in DMF with stirring for 10-60 minutes at a temperature between about 20-25° C., then precipitating by adding acetone, diethylether or n-hexanes and stirring for another 10-60 minutes at this temperature. The solid so formed is isolated by filtration. The material is dried under reduced pressure at a temperature between about 20° C. to about 80° C., preferably at 50° C. for 15 hours. The product obtained following this procedure is valacyclovir hydrochloride in form XII according to x-ray diffraction analysis.

The present invention provides a method for producing valacyclovir hydrochloride in form XIII which comprises the step of dissolving valacyclovir hydrochloride in DMF with stirring for 10-60 minutes at a temperature between about 20-25° C. and cooling to 0-5° C., then precipitating by adding acetone and stirring for another 10-60 minutes at this temperature. The solid so formed is isolated by filtration. The material is dried under reduced pressure at a temperature between about 20° C. to about 80° C., preferably at 50° C. for 15 hours. The product obtained following this procedure is valacyclovir hydrochloride in form XIII according to x-ray diffraction analysis.

The present invention provides a method for producing valacyclovir hydrochloride in form XMV which comprises the step of dissolving valacyclovir hydrochloride in methanol with stirring for 10-60 minutes at a temperature between about 40-80° C., preferably at 65° C. then precipitating by adding n-hexanes and stirring for another 10-60 minutes while cooling to ambient temperature. The solid so formed is isolated by filtration. The material is dried under reduced pressure at a temperature between about 20° C. to about 80° C., preferably at 50° C. for 15 hours. The product obtained following this procedure is valacyclovir hydrochloride in form XIV according to x-ray diffraction analysis.

EXAMPLES

Preparation of Crystalline Forms of Valacyclovir Hydrochloride

Example 1

Valacyclovir hydrochloride (1.0 g) was dissolved in DMF (5.0 mL) with stirring for 15-20 minutes at room temperature and cooled to 0° C. Then it was precipitated with ethyl acetate (20.0 mL). After stirring another 15-20 minutes at this temperature, the crystals were filtered and dried at 50° C. for 15 hours to give valacyclovir hydrochloride form VIR.

Water content (K.F.): 1.4502%.

Example 2

Valacyclovir hydrochloride (1.0 g) was dissolved in methanol (8.0 mL) with stirring for 15-20 minutes at reflux temperature and cooled to 0° C. Then it was precipitated with n-hexanes (20.0 mL) at this temperature. After stirring 15-20 minutes at 0° C., the crystals were filtered and dried at 50° C. for 15 hours to give valacyclovir hydrochloride form IX.

Water content (K.F.): 6.6874%.

Example 3

Valacyclovir hydrochloride (1.0 g) was dissolved in DMF (5.0 mL) with stirring for 15-20 minutes at room temperature and precipitated with acetone (20.0 mL) at 22-24° C. After stirring 15-20 minutes at this temperature, the crystals were filtered and dried at 50° C. for 15 hours to give valacyclovir hydrochloride form X.

Water content (K.F.): 5.8720%.

Example 4

Valacyclovir hydrochloride (1.0 g) was dissolved in DMF (5.0 mL) with stirring for 15-20 minutes at room temperature and precipitated with ethyl acetate (20.0 mL) at 22-24° C.

After stirring 15-20 minutes at this temperature the crystals were filtered and dried at 50° C. for 15 hours to give valacyclovir hydrochloride form XI.
Water content (K.F.): 1.8328%.

Example 5

Valacyclovir hydrochloride (1.0 g) was dissolved in DMF (5.0 mL) with stirring for 15-20 minutes at room temperature and precipitated with diethylether (20.0 mL) at 22-24° C. After stirring 15-20 minutes at this temperature the crystals were filtered and dried at 50° C. for 15 hours to give valacyclovir hydrochloride form XII.
Water content (K.F.): 0.8583%.

Example 6

Valacyclovir hydrochloride (1.0 g) was dissolved in DMF (5.0 mL) with stirring for 15-20 minutes at room temperature and precipitated with n-hexanes (20.0 mL) at 22-24° C. After stirring 15-20 minutes at this temperature the crystals were filtered and dried at 50° C. for 15 hours to give valacyclovir hydrochloride form XII.
Water content (K.F.): 0.6872%.

Example 7

Valacyclovir hydrochloride (1.0 g) was dissolved in methanol (8.0 mL) with stirring for 15-20 minutes at reflux temperature and precipitated immediately by the addition of acetone (20.0 mL). After stirring 15-20 minutes at ambient temperature, the crystals were filtered and dried at 50° C. for 15 hours to give valacyclovir hydrochloride form XII.
Water content (K.F.): 6.7046%.

Example 8

Valacyclovir hydrochloride (1.0 g) was dissolved in methanol (8.0 mL) with stirring for 15-20 minutes at reflux temperature, cooled to room temperature and precipitated by the addition of diethylether (20.0 mL). After stirring 15-20 minutes at ambient temperature, the crystals were filtered and dried at 50° C. for 15 hours to give valacyclovir hydrochloride form XII.
Water content (K.F.): 7.7137%.

Example 9

Valacyclovir hydrochloride (1.0 g) was dissolved in DMF (5.0 mL) with stirring for 15-20 minutes at room temperature and cooled to 0° C. Then it was precipitated with acetone (20.0 mL). After stirring 15-20 minutes at this temperature, the crystals were filtered and dried at 50° C. for 15 hours to give valacyclovir hydrochloride form XIII.
Water content (K.F.): 4.4783%.

Example 10

Valacyclovir hydrochloride (1.0 g) was dissolved in methanol (8.0 mL) with stirring for 15-20 minutes at reflux temperature and precipitated immediately by the addition of n-hexanes (20.0 mL). After stirring 15-20 minutes at ambient temperature, the crystals were filtered and dried at 50° C. for 15 hours to give valacyclovir hydrochloride form XIV.
Water content (K.F.): 6.5580%.

What is claimed is:

1. A method of producing valacyclovir hydrochloride in crystal form VIII, comprising the steps of:
    dissolving valacyclovir hydrochloride in dimethylformamide at a temperature ranging from about 20 to 25° C.,
    cooling the solution to a temperature ranging from about 0 to 5° C. and precipitating valacyclovir hydrochloride by adding ethyl acetate,
    isolating valacyclovir hydrochloride from the mixture in form VIII, and
    optionally drying isolated valacyclovir hydrochloride.

2. A method for producing valacyclovir hydrochloride in crystal form IX, comprising the steps of:
    dissolving valacyclovir hydrochloride in methanol at a temperature ranging from about 20 to 80° C.,
    cooling the solution to a temperature ranging from about 0 to 5° C. and precipitating valacyclovir hydrochloride by adding n-hexanes,
    isolating valacyclovir hydrochloride from the mixture in form IX, and
    optionally drying the isolated valacyclovir hydrochloride.

3. A method for producing valacyclovir hydrochloride crystals according to claim 2, wherein the dissolving step is conducted at a temperature of about 65° C.

4. A method for producing valacyclovir hydrochloride in crystal form X, comprising the steps of:
    dissolving valacyclovir hydrochloride in dimethylformamide at a temperature ranging from about 20 to 25° C.,
    precipitating the same by adding acetone,
    isolating valacyclovir hydrochloride from the mixture in form X, and
    optionally drying the isolated valacyclovir hydrochloride.

5. A method for producing valacyclovir hydrochloride in crystal form XI, comprising the steps of:
    dissolving valacyclovir hydrochloride in dimethylformamide at a temperature ranging from about 20 to 25° C.,
    precipitating the same by adding ethyl acetate,
    isolating valacyclovir hydrochloride from the mixture in form XI, and
    optionally drying the isolated valacyclovir hydrochloride.

6. A method for producing valacyclovir hydrochloride in crystal form XII, comprising the steps of:
    dissolving valacyclovir hydrochloride in dimethylformamide at a temperature ranging from about 20 to 25° C.,
    precipitating the same by adding a reagent selected from the group consisting of n-hexanes and diethylether,
    isolating valacyclovir hydrochloride from the mixture in form XII, and
    optionally drying the isolated valacyclovir hydrochloride.

7. A method for producing valacyclovir hydrochloride in crystal form XIII, comprising the steps of:
    dissolving valacyclovir hydrochloride in dimethylformamide at a temperature ranging from about 20 to 25° C.,
    cooling the solution to a temperature ranging from about 0 to 5° C. and precipitating the same by adding acetone,
    isolating valacyclovir hydrochloride from the mixture in form XIII, and
    optionally drying the isolated valacyclovir hydrochloride.

8. A method for producing valacyclovir hydrochloride in crystal form XIV, comprising the steps of:
    dissolving valacyclovir hydrochloride in methanol at a temperature ranging from about 40 to 80° C.,
    cooling the solution to about ambient temperature and precipitating the same by adding n-hexanes,
    isolating valacyclovir hydrochloride from the mixture in form XIV, and
    optionally drying the isolated valacyclovir hydrochloride.

9. A method for producing valacyclovir hydrochloride crystals according to claim 8, wherein the dissolving step is conducted at a temperature about 65° C.

10. A method according to claim 1, wherein the isolated sample is dried at a reduced pressure and at a temperature ranging from 20° C. to 80° C. for a duration of 1 to 24 hours to yield crystals having water content of about 0.5% to 3% according to Karl Fischer analysis method.

11. A method for producing valacyclovir hydrochloride in crystal form XII, comprising the steps of:
dissolving valacyclovir hydrochloride in methanol at about reflux temperature,
precipitating the same by adding a reagent selected from the group consisting of acetone and diethylether,
isolating valacyclovir hydrochloride from the mixture in form XII, and
optionally drying the isolated valacyclovir hydrochloride.

12. A method according to claim 2 wherein the isolated sample is dried at a reduced pressure, and at a temperature ranging from 20° C. to 80° C. for a duration of 1 to 24 hours to yield crystals having water content of about 6% to 10% according to Karl Fischer analysis method.

13. A method according to claim 4 wherein the isolated sample is dried at a reduced pressure, and at a temperature ranging from 20° C. to 80° C. for a duration of 1 to 24 hours to yield crystals having water content of about 3% to 7% according to Karl Fischer analysis method.

14. A method according to claim 5 wherein the isolated sample is dried at a reduced pressure, and at a temperature ranging from 20° C. to 80° C. for a duration of 1 to 24 hours to yield crystals having water content of about 1% to 3% according to Karl Fischer analysis method.

15. A method according to claim 2 wherein the isolated sample is dried at a reduced pressure, and at a temperature ranging from 20° C. to 80° C. for a duration of 1 to 24 hours to yield crystals having water content of about 0.5% to 9% according to Karl Fischer analysis method.

16. A method according to claim 11 wherein the isolated sample is dried at a reduced pressure, and at a temperature ranging from 20° C. to 80° C. for a duration of 1 to 24 hours to yield crystals having water content of about 0.5% to 9% according to Karl Fischer analysis method.

17. A method according to claim 7 wherein the isolated sample is dried at a reduced pressure, and at a temperature ranging from 20° C. to 80° C. for a duration of 1 to 24 hours to yield crystals having water content of about 3% to 5% according to Karl Fischer analysis method.

18. A method according to claim 8 wherein the isolated sample is dried at a reduced pressure, and at a temperature ranging from 20° C. to 80° C. for a duration of 1 to 24 hours to yield crystals having water content of about 6% to 9% according to Karl Fischer analysis method.

* * * * *

UNITED STATES PATENT AND TRADEMARK OFFICE
CERTIFICATE OF CORRECTION

PATENT NO. : 7,786,302 B2  
APPLICATION NO. : 10/558243  
DATED : August 31, 2010  
INVENTOR(S) : Tuncer Aslan It is certified that error appears in the above-identified patent and that said Letters Patent is hereby corrected as shown below:

Title Page:

In (73) Assignee, please correct the Assignee's name to read as follows:

(73) Assignee: ~~Eczacibasi~~ Zentiva Kimyasal Urunler Sanayi Ve Ticaret A.S.

Signed and Sealed this

Ninth Day of November, 2010

David J. Kappos  
*Director of the United States Patent and Trademark Office*